US00PP32683P3

(12) United States Plant Patent
Matsumoto

(10) Patent No.: US PP32,683 P3
(45) Date of Patent: Dec. 22, 2020

(54) ***VERBENA* PLANT NAMED 'RIKAV52102'**

(50) Latin Name: *Verbena hybrida*
Varietal Denomination: RIKAV52102

(71) Applicant: Rika Matsumoto, Omihachiman (JP)

(72) Inventor: Rika Matsumoto, Omihachiman (JP)

(73) Assignee: PLANT 21 LLC, Bonsall, CA (US)

( * ) Notice: Subject to any disclaimer, the term of this patent is extended or adjusted under 35 U.S.C. 154(b) by 0 days.

(21) Appl. No.: 16/873,483

(22) Filed: Apr. 17, 2020

(65) Prior Publication Data

US 2020/0367400 P1 Nov. 19, 2020

(30) Foreign Application Priority Data

May 17, 2019 (CA) ..... PBR 19-9880

(51) Int. Cl.
*A01H 5/02* (2018.01)
*A01H 6/86* (2018.01)

(52) U.S. Cl.
USPC ..... Plt./308
CPC ..... *A01H 6/86* (2018.05)

(58) Field of Classification Search
USPC ..... Plt./308
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Verbena* plant named 'RIKAV52102', characterized by its outwardly spreading and mounding plant habit; vigorous growth habit; freely branching habit; dark green-colored leaves; freely flowering habit; relatively large dark and light red purple bi-colored flowers that are held above and beyond the foliar plane; and relative tolerance to Powdery Mildew (*Podosphaera xanthii*).

1 Drawing Sheet

Botanical designation: *Verbena hybrida.*
Cultivar denomination: 'RIKAV52102'.

CROSS-REFERENCE TO A RELATED APPLICATION AND STATEMENT REGARDING PRIOR DISCLOSURES BY INVENTOR/APPLICANT

This application claims priority to a Canadian Plant Breeders' Rights application filed on May 17, 2019, application number 19-9880. There have been no offers for sale anywhere in the world prior to the effective filing date of this Application and no accessibility to one of ordinary skill in the art could have been derived from the printed Plant Breeder's Rights documents.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor. Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Verbena* plant, botanically known as *Verbena hybrida*, and hereinafter referred to by the name 'RIKAV52102'.

The new *Verbena* plant is a product of a planned breeding program conducted by the Inventor in Higashiomi, Shiga, Japan and Bonsall, Calif. The objective of the breeding program is to create new vigorous and freely-branching

*Verbena* plants with numerous flowers and tolerance to Powdery Mildew (*Podosphaera xanthii*).

The new *Verbena* plant originated from a cross-pollination made by the Inventor on May 20, 2016 in Higashiomi, Shiga, Japan of a proprietary seedling selection of *Verbena hybrida* identified as code number 12V278-01mutant1, not patented, as the female, or seed, parent with a proprietary seedling selection of *Verbena hybrida* identified as code number 15V421-05, not patented, as the male, or pollen, parent. The new *Verbena* plant was discovered and selected by the Inventor as a single flowering plant from within the progeny of the stated cross-pollination in a controlled greenhouse environment in Bonsall, Calif. on Jun. 6, 2017.

Asexual reproduction of the new *Verbena* plant by vegetative terminal cuttings in a controlled environment in Bonsall, Calif. since Jun. 19, 2017, has shown that the unique features of this new *Verbena* plant are stable and reproduced true to type in successive generations.

SUMMARY OF THE INVENTION

Plants of the new *Verbena* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'RIKAV52102'. These characteristics in combination distinguish 'RIKAV52102' as a new and distinct *Verbena* plant:

1. Outwardly spreading and mounding plant habit.
2. Vigorous growth habit.
3. Freely branching habit.
4. Dark green-colored leaves.

5. Freely flowering habit.
6. Relatively large dark and light red purple bi-colored flowers that are held above and beyond the foliar plane.
7. Relatively tolerant to Powdery Mildew (*Podosphaera xanthii*).

Plants of the new *Verbena* can be compared to plants of the female parent selection. Plants of the new *Verbena* differ primarily from plants of the female parent selection in the following characteristics:

1. Plants of the new *Verbena* are more vigorous than plants of the female parent selection.
2. Plants of the new *Verbena* are more freely branching than plants of the female parent selection.
3. Plants of the new *Verbena* are more freely flowering than plants of the female parent selection.
4. Plants of the new *Verbena* are more tolerant to Powdery Mildew than plants of the female parent selection.

Plants of the new *Verbena* can be compared to plants of the male parent selection. Plants of the new *Verbena* differ primarily from plants of the male parent selection in the following characteristics:

1. Plants of the new *Verbena* are more vigorous than plants of the male parent selection.
2. Plants of the new *Verbena* are more freely branching than plants of the male parent selection.
3. Plants of the new *Verbena* are more tolerant to Powdery Mildew than plants of the male parent selection.

Plants of the new *Verbena* can be compared to plants of the *Verbena hybrida* 'Lan Reda07', disclosed in U.S. Plant Pat. No. 18,986. In side-by-side comparisons, plants of the new *Verbena* differ primarily from plants of 'Lan Reda07' in the following characteristics:

1. Plants of the new *Verbena* are more vigorous than plants of 'Lan Reda07'.
2. Plants of the new *Verbena* have larger flowers than plants of 'Lan Reda07'.
3. Plants of the new *Verbena* and 'Lan Reda07' differ in flower color as plants of the new *Verbena* have dark and light red purple bi-colored flowers whereas plants of 'Lan Reda07' have red-colored flowers.
4. Plants of the new *Verbena* are more tolerant to Powdery Mildew than plants of 'Lan Reda07'.

Plants of the new *Verbena* can be compared to plants of the *Verbena hybrida* 'Usbenal5', disclosed in U.S. Plant Pat. No. 14,851. In side-by-side comparisons, plants of the new *Verbena* differ primarily from plants of 'Usbenal5' in the following characteristics:

1. Plants of the new *Verbena* are more mounding than and not as upright as plants of 'Usbenal5'.
2. Plants of the new *Verbena* are more freely flowering than plants of 'Usbenal5'.
3. Plants of the new *Verbena* and 'Usbenal5' differ in flower color as plants of the new *Verbena* have dark and light red purple bi-colored flowers whereas plants of 'Usbenal5' have purple-colored flowers.
4. Plants of the new *Verbena* are more tolerant to Powdery Mildew than plants of 'Usbenal5'.

BRIEF DESCRIPTION OF THE PHOTOGRAPHS

The accompanying colored photographs illustrate the overall appearance of the new *Verbena* plant showing the colors as true as it is reasonably possible to obtain in colored reproductions of this type. Colors in the photographs may differ slightly from the color values cited in the detailed botanical description which accurately describe the colors of the new *Verbena* plant.

At the top of the photographic sheet (FIG. 1) is a side perspective view of a typical flowering plant of 'RIKAV52102' grown in a container and at the bottom of the photographic sheet is a close-up view of a typical flowering plant of 'RIKAV52102'.

DETAILED BOTANICAL DESCRIPTION

The aforementioned photographs and following observations and measurements describe plants grown during the spring in 15.25-cm containers in a polyethylene-covered greenhouse in St. Thomas, Ontario, Canada and under cultural practices typical of commercial *Verbena* production. During the production of the plants, day temperatures averaged 27° C. and night temperatures averaged 15° C. Plants were pinched when planted and were nine weeks from planting rooted cuttings when the photographs and description were taken. In the following description, color references are made to The Royal Horticultural Society Colour Chart, 2007 Edition, except where general terms of ordinary dictionary significance are used.

Botanical classification: *Verbena hybrida* 'RIKAV52102'.

Parentage:

*Female, or seed, parent*.—Proprietary seedling selection of *Verbena hybrida* identified as code number 12V278-01mutant1, not patented.

*Male, or pollen, parent*.—Proprietary seedling selection of *Verbena hybrida* identified as code number 15V421-05, not patented.

Propagation:

*Type cutting*.—Vegetative terminal cuttings.

*Time to initiate roots, summer*.—About three to four days at temperatures ranging from about 16° C. to 29° C.

*Time to initiate roots, winter*.—About four to five days at temperatures ranging from about 16° C. to 21° C.

*Time to produce a rooted plant, summer*.—About 15 days at temperatures ranging from about 16° C. to 29° C.

*Time to produce a rooted plant, winter*.—About 20 days at temperatures ranging from about 16° C. to 21° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Outwardly spreading and mounding to eventually trailing plant habit; freely branching habit with about eight primary lateral branches each with about ten secondary lateral branches developing per plant; pinching enhances branching potential; dense and bushy plant habit; vigorous growth habit and moderate growth rate.

*Plant height*.—About 17.3 cm.

*Plant diameter* (*spread*).—About 63.8 cm.

Lateral branch description:

*Length*.—About 18.5 cm.

*Diameter*.—About 2.2 mm.

*Internode length*.—About 3 cm.

*Orientation*.—Initially upright then outwardly spreading to turning upright distally.

*Strength*.—Moderately strong to strong.

*Texture and luster*.—Moderately pubescent; slightly glossy.

*Color, developing*.—Close to 144A.

*Color, developed*.—Close to 146B.

Leaf description:

*Arrangement*.—Opposite, simple.

*Length*.—About 4.6 cm.

*Width*.—About 3.3 cm.

*Shape*.—Deltoid, elongated.

*Apex*.—Broadly acute.

*Base*.—Truncate to obtuse.

*Margin*.—Crenate.

*Texture and luster, upper surface*.—Sparsely to moderately pubescent; matte.

*Texture and luster, lower surface*.—Densely pubescent; matte.

*Venation pattern*.—Pinnate; reticulate.

*Color*.—Developing leaves, upper surface: Close to 147A. Developing leaves, lower surface: Close to 146B. Fully expanded leaves, upper surface: Close to 147B; venation, close to 147B. Fully expanded leaves, lower surface: Close to 148D; venation, close to 148D.

*Petioles*.—Length: About 4.9 mm. Diameter: About 3.1 mm. Strength: Moderately strong. Texture and luster, upper and lower surfaces: Densely pubescent; matte. Color, upper surface: Close to 145C. Color, lower surface: Close to 144D.

Flower description:

*Flower arrangement and habit*.—Sessile salverform flowers arranged in upright hemispherical terminal racemes; flowers face upward or outwardly; freely flowering habit with about 24 flowers developing per inflorescence and typically more than 1,350 flowers developing per plant.

*Natural flowering season*.—Plants flower continuously from spring until frost in Ontario, Canada; early flowering habit, plants begin flowering about five weeks after planting.

*Flower longevity*.—Flowers last about five days on the plant; flowers not persistent.

*Fragrance*.—None detected.

*Inflorescence height*.—About 3.7 cm.

*Inflorescence diameter*.—About 5.9 cm.

*Flower buds*.—Length: About 1.5 cm. Diameter: About 3 mm. Shape: Elongated oblong. Texture and luster: Densely pubescent; matte. Color: Close to 71C.

*Flower diameter*.—About 2 cm.

*Flower depth (height)*.—About 2.8 cm.

*Throat diameter*.—About 2 mm.

*Tube length*.—About 1.9 cm.

*Tube diameter, proximally*.—About 1.8 mm.

*Corolla*.—Arrangement: Single whorl of five fused petals fused towards the base into a slender narrow tube. Petal lobe length: About 9 mm. Petal lobe width: About 8 mm. Petal lobe shape: Roughly cordate. Petal lobe apex: Emarginate. Petal margin: Entire; moderately undulate. Petal texture and luster, upper and lower surfaces: Smooth, glabrous; matte. Throat texture and luster: Moderately pubescent; matte. Tube texture and luster: Moderately pubescent; matte. Color: Petal lobes, when opening, upper surface: Upper two petals, darker than N57A; lower three petals, close to N155B overlain with close to N57C to N57D. Petal lobes, when opening, lower surface: Upper two petals, close to N57B; lower three petals, close to N155B overlain with close to N57D. Petal lobes, fully opened, upper surface: Upper two petals, darker than N57A; lower three petals, close to N155B overlain with close to N57C to N57D; venation, same as lamina; with development, upper two petals become closer to 69D overlain with close to 68C and 67D and lower three petals become closer to NN155B. Petal lobes, fully opened, lower surface: Upper two petals, close to 69B and 62C; lower three petals, close to N155B; venation, same as lamina; with development, upper two petals become closer to N155B overlain with 62D and lower three petals, become closer to NN155B. Throat: Close to 145D; venation, close to 145D. Tube: Close to 145D; venation, close to 145D.

*Calyx*.—Arrangement: Single whorl of five fused sepals fused towards the base into a slender tube. Length: About 1.3 cm. Diameter: About 2 mm. Sepal length: About 1.3 cm. Sepal width: About 1 mm. Sepal shape: Narrowly lanceolate. Sepal apex: Narrowly acute. Sepal margin: Entire. Sepal texture and luster, upper and lower surfaces: Densely pubescent; matte. Sepal color, upper and lower surfaces: Close to 137D.

*Peduncles*.—Length: About 2.9 cm. Diameter: About 1.8 mm. Strength: Moderately strong. Aspect: Mostly upright. Texture and luster: Moderately pubescent; matte. Color: Close to 146B.

*Reproductive organs*.—Stamens: Quantity and arrangement: Four per flower, filaments partially adnate to corolla tube. Filament length: About 1.1 cm. Filament color: Close to 145C. Anther size: About 1 mm by 1 mm. Anther shape: Oval. Anther color: Close to 151D. Pollen amount: Scarce to moderate. Pollen color: Close to 9C. Pistils: Quantity: One per flower. Pistil length: About 1.8 cm. Stigma shape: Bi-parted. Stigma diameter: About 2 mm by 1 mm. Stigma color: Close to 144A. Style length: About 1.5 cm. Style color: Close to 145C. Ovary color: Close to 144A. Fruits and seeds: To date, fruit and seed development have not been observed on plants of the new *Verbena*.

Temperature tolerance: Plants of the new *Verbena* have been observed to tolerate temperatures from about 2° C. to about 40° C. and are suitable for USDA Hardiness Zones 8a to 11b.

Pathogen & pest resistance: Plants of the new *Verbena* have been observed to be relatively tolerant to Powdery Mildew (*Podosphaera xanthii*). To date, plants of the new *Verbena* have not been observed to be resistant to pests and other pathogens common to *Verbena* plants.

It is claimed:

1. A new and distinct *Verbena* plant named 'RIKAV52102' as illustrated and described.

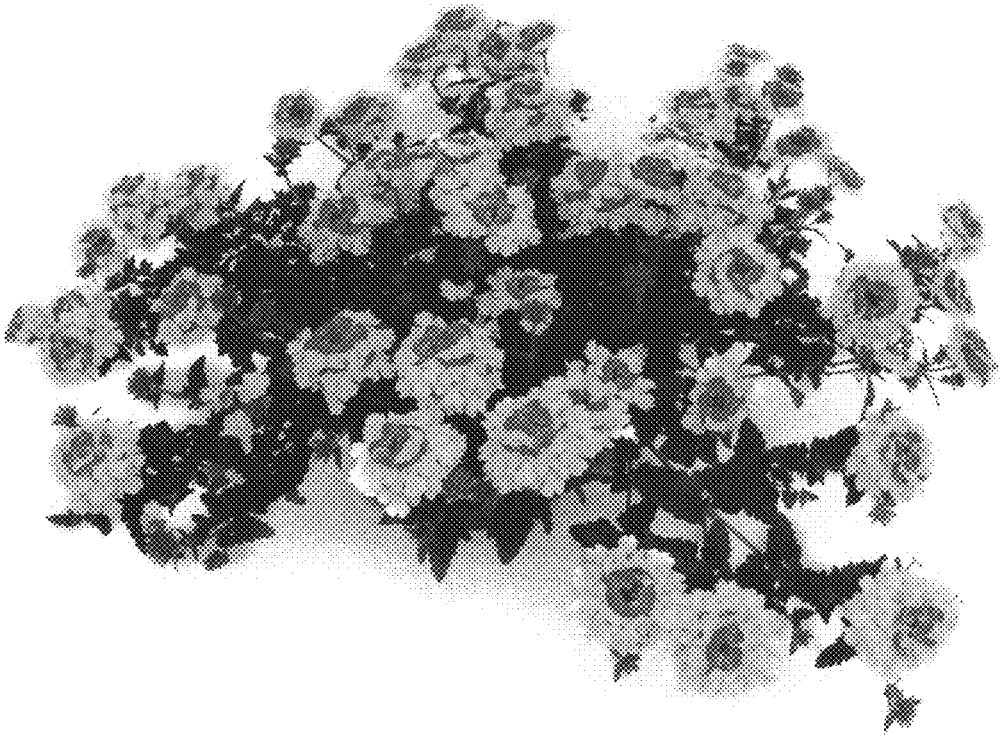
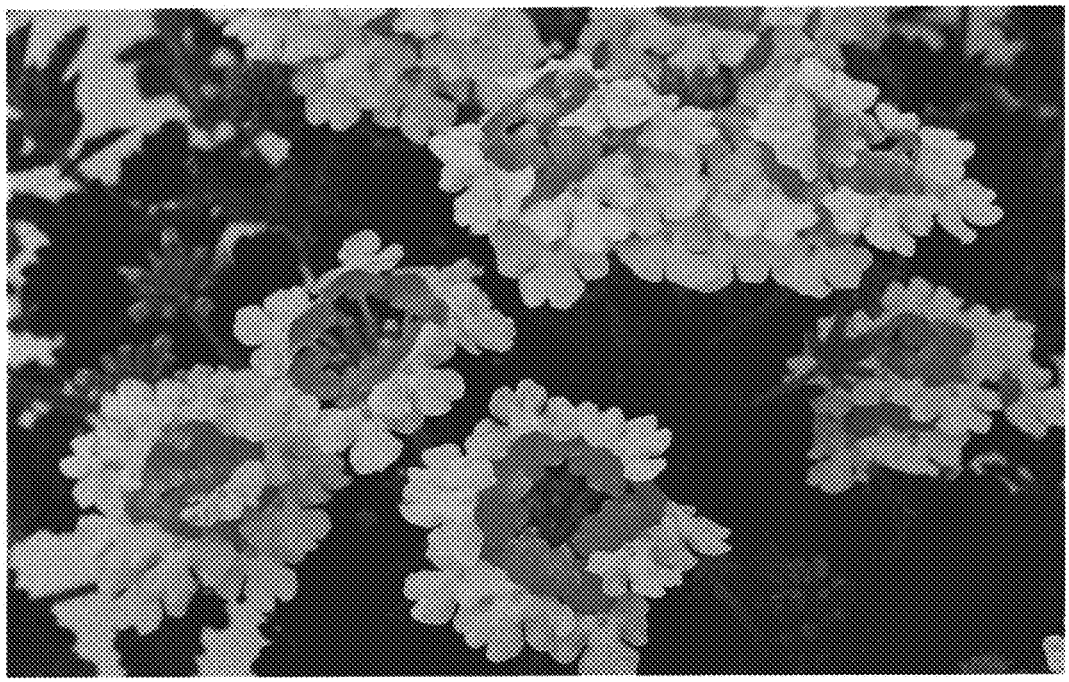

* * * * *